United States Patent
Kanou et al.

(10) Patent No.: US 7,114,889 B2
(45) Date of Patent: Oct. 3, 2006

(54) POWDERY PARTICLE CONVEYING SYSTEM AND ROOTS BLOWER OPERATING METHOD

(75) Inventors: Osamu Kanou, Saitama (JP);
Yoshinori Miyashita, Saitama (JP);
Shigemi Fujisawa, Saitama (JP);
Yoshiaki Hamada, Saitama (JP);
Yoshio Nakada, Saitama (JP); Akihiro Tanaka, Saitama (JP); Hiroomi Uehara, Kanagawa (JP)

(73) Assignee: Nisshin Seifun Group Inc., Tokyo (JP)

( * ) Notice: Subject to any disclaimer, the term of this patent is extended or adjusted under 35 U.S.C. 154(b) by 41 days.

(21) Appl. No.: 10/397,630

(22) Filed: Mar. 25, 2003

(65) Prior Publication Data

US 2003/0185636 A1    Oct. 2, 2003

(30) Foreign Application Priority Data

Mar. 27, 2002 (JP) ............................. 2002-088634
Feb. 4, 2003 (JP) ............................. 2003-026815

(51) Int. Cl.
*B65G 53/66* (2006.01)

(52) U.S. Cl. ........................................ 406/14; 406/156
(58) Field of Classification Search ................. 406/14, 406/1, 2, 30, 155, 156
See application file for complete search history.

(56) References Cited

U.S. PATENT DOCUMENTS

| | | | | | |
|---|---|---|---|---|---|
| 4,368,678 | A | * | 1/1983 | Ulveling | 110/347 |
| 4,402,635 | A | * | 9/1983 | Maruo | 406/14 |
| 4,420,279 | A | * | 12/1983 | Easley, Jr. | 406/14 |
| 4,936,870 | A | * | 6/1990 | Baumann et al. | 48/197 R |
| 4,946,317 | A | * | 8/1990 | Liu et al. | 406/46 |
| 5,040,929 | A | * | 8/1991 | Paul et al. | 406/33 |
| 5,143,485 | A | * | 9/1992 | Faas et al. | 406/14 |
| 5,354,152 | A | * | 10/1994 | Reinhardt et al. | 406/3 |
| 5,549,421 | A | * | 8/1996 | Reinhardt et al. | 406/3 |
| 5,865,568 | A | * | 2/1999 | Relin et al. | 406/85 |
| 6,447,215 | B1 | * | 9/2002 | Wellmar | 406/11 |

* cited by examiner

*Primary Examiner*—Khoi H. Tran
(74) *Attorney, Agent, or Firm*—Townsend and Townsend and Crew LLP

(57) ABSTRACT

A powdery particle conveying system is provided in which electric power consumption can be saved when powdery particles are conveyed by use of a roots blower. In the case where the powdery particles are conveyed to a reservoir tank near the roots blower, the frequency of a power source of a roots blower driving motor is reduced, thereby reducing an output of the roots blower. In contrast, in the case where the powdery particles are conveyed to a remote reservoir tank, a voltage of a commercial frequency is applied to the motor.

8 Claims, 5 Drawing Sheets

POWDERY PARTICLE CONVEYING SYSTEM AND ROOTS BLOWER OPERATING METHOD

BACKGROUND OF THE INVENTION

1. Field of the Invention

The present invention relates to a powdery particle conveying system which conveys powdery particles such as flour or livestock feed to a reservoir tank and a roots blower operating method for use in the system.

2. Description of the Prior Art

An explanation will be made by way of conveyance of flour in a flour mill. In the flour mill, numerous kinds of flour are milled, and then they are reserved in different tanks according to the kinds of flour. The conveyance to a reservoir tank is carried out by using a roots blower. In the roots blower, a fan is rotated by a motor, so as to generate a compressed air current, which is press-fed into a conveying pipe, and thus the flour in the air current is conveyed to a predetermined reservoir tank.

One roots blower or a plurality of roots blowers are installed in the flour mill. The conveying pipe extends from the roots blower to the reservoir tank. Switch valves are disposed at branch points from the conveying pipe to the reservoir tanks. A conveying channel to each of the reservoir tanks is defined by switching the switch valves, and consequently, the flour is conveyed to a desired reservoir tank.

Specifically, as illustrated in FIG. 1, a rotary valve 42 having an air sealing function is disposed under a hopper 40 for holding the milled flour therein, and further is connected to a conveying pipe 46. A measuring unit 41 is disposed downstream of the hopper 40. In the meantime, there is provided a roots blower 44. Powdery particles are press-fed from the hopper 40 through the conveying pipe 46 by a compressed air current generated by the roots blower 44. A plurality of reservoir tanks 30 are installed at positions apart from the hopper 40. Switch valves 48 are disposed at branch points from the conveying pipe 46 to the reservoir tanks 30. The flour is conveyed to each of the reservoir tanks 30 by operating the switch valves 48.

The roots blower 44 is required to have a sufficient capacity to convey the flour to any of the reservoir tanks 30. Therefore, the roots blower 44 is designed to have such a capacity or volume as to convey the flour to a reservoir tank 30B located at a remotest or highest position among the reservoir tanks 30, that is, a reservoir tank requiring the largest conveying load.

In the above-described prior art powdery particle conveying system, the roots blower having such a capacity as to sufficiently convey the powdery particles even to the reservoir tank 30B located at the remotest position is operated with its rated output, and thus the powdery particles are conveyed to all of the reservoir tanks. That is to say, the powdery particle conveying system is operated with the roots blower driving motor at the same frequency of a power source even in the case where the flour is conveyed to a reservoir tank 30A located at a position nearest the roots blower 44 as a frequency of the power source at which the flour is conveyed to the reservoir tank 30B, and therefore energy is wastefully used. In this case, the conveying load. In contrast, the rotating output of the motor is reduced so as to convey the powdery particles while reducing an electric power consumption in the case of the small conveying load; thus reducing energy consumption.

Other methods for changing the output of the roots blower include a method in which a conveying state is observed while reducing the speed of the roots blower driving motor according to the conveying load, so as to change the speed to a lowest speed at which the conveyance can be maintained; and a method in which the output of the roots blower required for each of the conveying loads is previously calculated, and then it is stored in a memory device or the like, so that the output of the roots blower with respect to a conveying load according to powdery particles to be conveyed or conveying conditions is read out of the memory device or the like when the powdery particles to be conveyed or the conveying conditions are input, and thus the output of the roots blower is automatically changed.

A similar problem arises not only because of the difference in conveying distance but also the conveying quantity or kind of powdery particles to be conveyed (for example, flour, wheat bran, flour grains and the like) or the magnitude of a conveying load such as a pressure loss on a conveying channel (for example, the bend of the conveying channel, the number of switch valves, the property of the inner surface of the conveying pipe, i.e., a surface roughness, and the like).

SUMMARY OF THE INVENTION

It is an object of the present invention to solve the above problems observed in the prior art. More specifically, the present invention provides a powdery particle conveying system which can convey powdery particles without any waste of energy according to a conveying load during the conveyance of the powdery particles and a roots blower operating method for use in the conveying system.

In order to achieve the above-described object, according to the present invention, an output of a roots blower is changed according to a conveying load during the conveyance of powdery particles, so that the roots blower is operated with a minimum output all times. For example, the frequency of the power source voltage of a roots blower driving motor is minimized as much as possible to change the output of the roots blower, thereby suppressing the rotating output of the motor. Consequently, the powdery particles can be sufficiently conveyed by operating the system with the same rated output as that in the prior art in the case of the large FIG. 5 is a circuit diagram illustrating the configuration of a speed control of a roots blower driving motor in the powdery particle conveying system illustrated in FIG. 4.

DETAILED DESCRIPTION OF THE PREFERRED EMBODIMENTS

The present invention will be described below by reference to the accompanying drawings.

Figure 1:
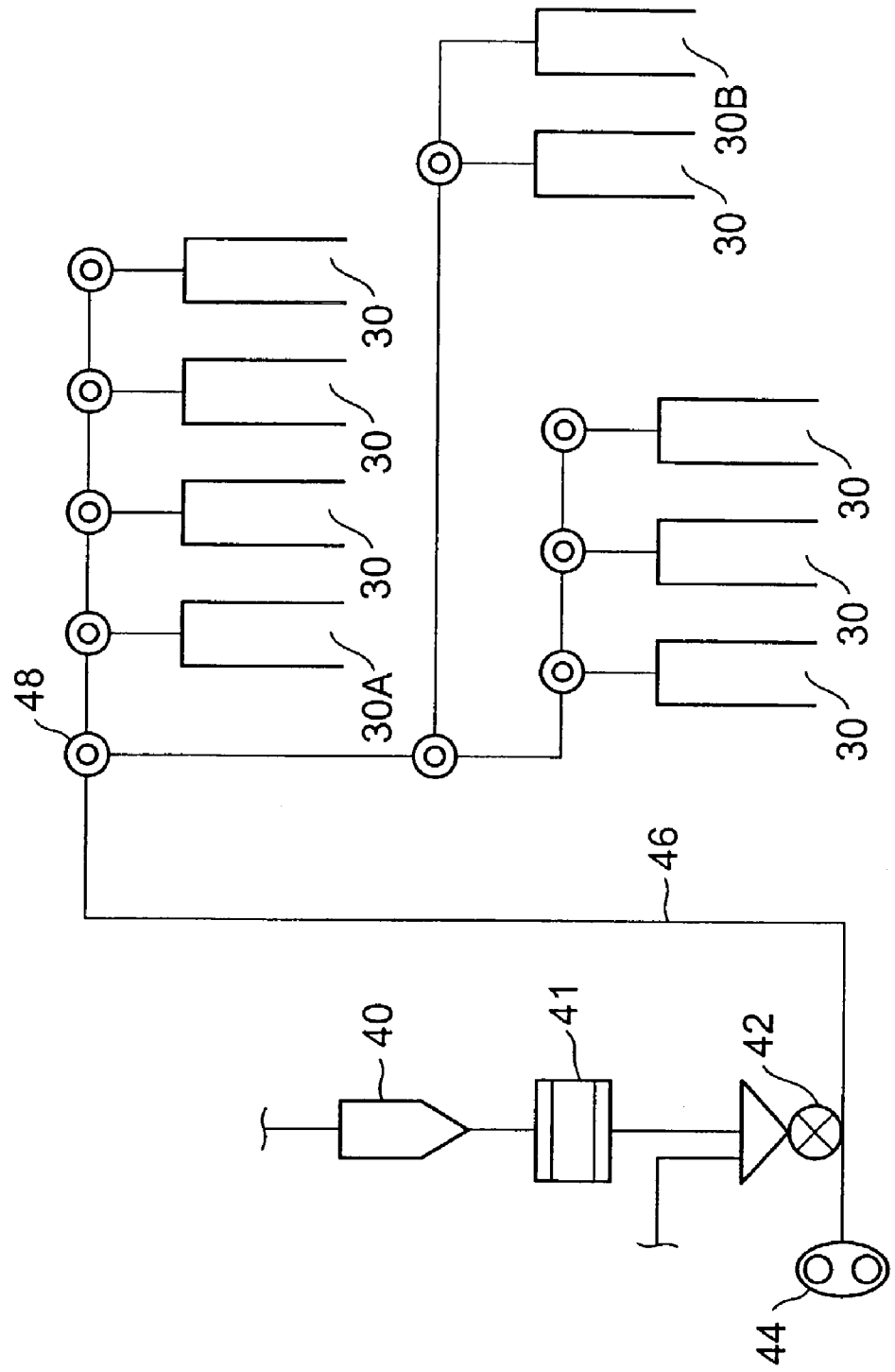
FIG. 1 is a diagram illustrating the general configuration of a powdery particle conveying system in the prior art.
Figure 2:
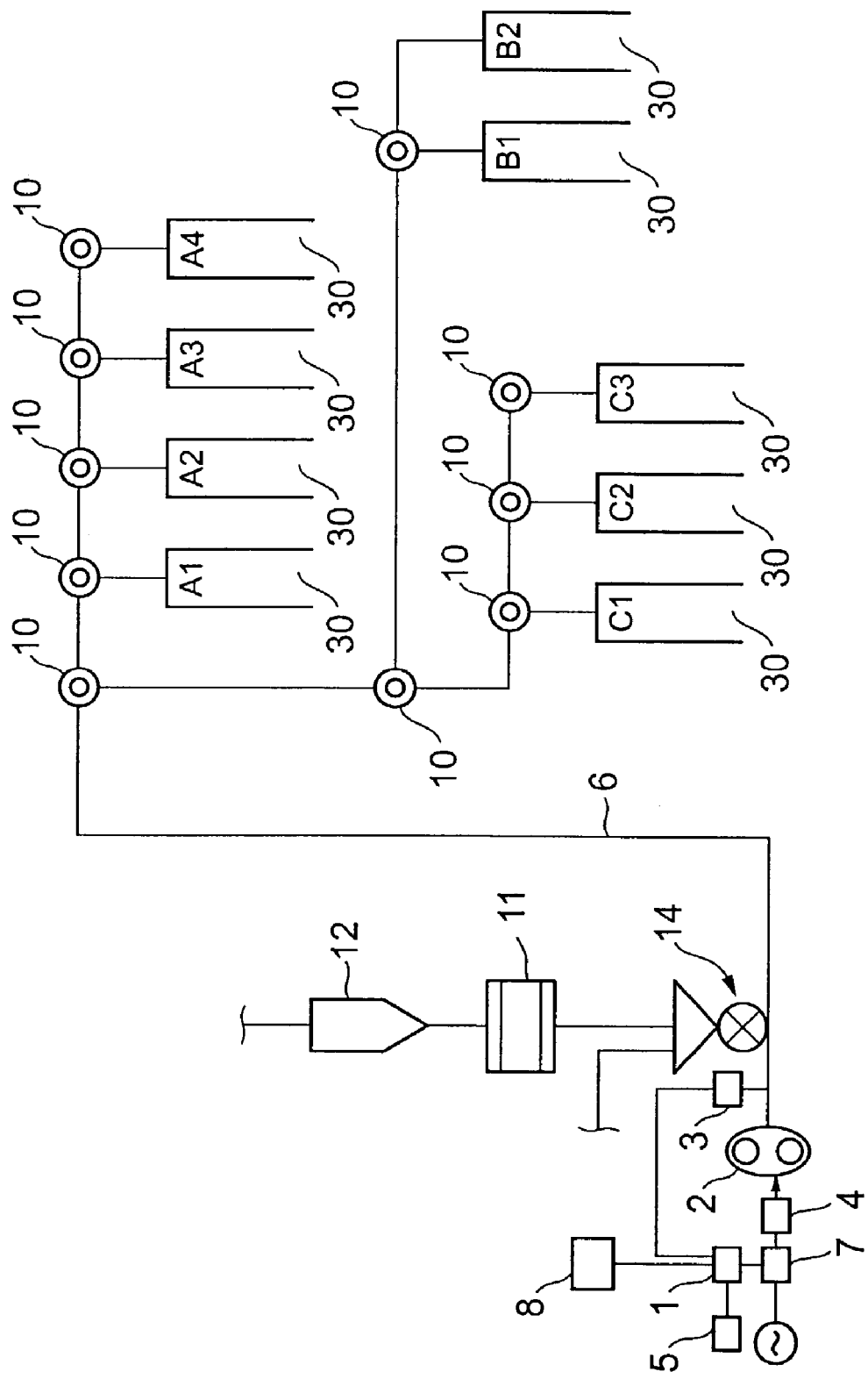
FIG. 2 is a diagram illustrating the general configuration of a powdery particle conveying system in an embodiment according to the present invention.

FIG. 2 illustrates the general configuration of a powdery particle conveying system in an embodiment according to the present invention.

In this powdery particle conveying system, powdery particles to be supplied from a hopper 12 serving as a reservoir are conveyed to a plurality of reservoir tanks 30 (A1 to A4, B1 and B2 and C1 to C3) installed at remote positions via a conveying pipe 6 on a compressed air flow generated by a roots blower 2, and then are stored in the reservoir tanks 30. The hopper 12 is disposed on the supply side and is connected to the conveying pipe 6 via a measuring unit 11 and a rotary valve 14 which is used for controlling the supply and sealing the air. The roots blower 2 is driven by a motor 4 to compress the air sucked through a suction pipe, and then feeds out a compressed air flow to the conveying pipe 6 connected onto a discharge side. The rotary valve 14 has the function of conveying the powdery particles, which have been fed into the conveying pipe 6, through the conveying pipe 6 without the powdery particles being injected onto the side of the hopper 12.

A pressure gauge 3 for measuring a pressure inside of the conveying pipe 6, that is, a discharge pressure of the roots blower 2, is connected to a joint point between the discharge side of the roots blower 2 and the rotary valve 14.

The conveying pipe 6 is branched to each of the reservoir tanks 30. A switch valve 10 for switching a channel for the powdery particles is provided at each branch point.

A variable-speed motor such as an induction motor or a synchronous motor is used as the motor 4 in the roots blower 2. It has a sufficient output to press-feed the powdery particles to the reservoir tank located at the remotest position, that is, the reservoir tank 30 (i.e., B2) requiring the largest conveying load. Electric power is supplied to the motor 4 via an inverter (i.e., an electric power frequency converter) 7 for converting the frequency of voltage of an electric power source. The inverter 7 can arbitrarily convert the frequency of the voltage of the electric power source to be applied to the motor 4. Incidentally, the motor 4 may be a motor with a continuously variable transmission such as a ring cone motor. In this case, a speed controller in place of the inverter 7 is required.

Figure 3:
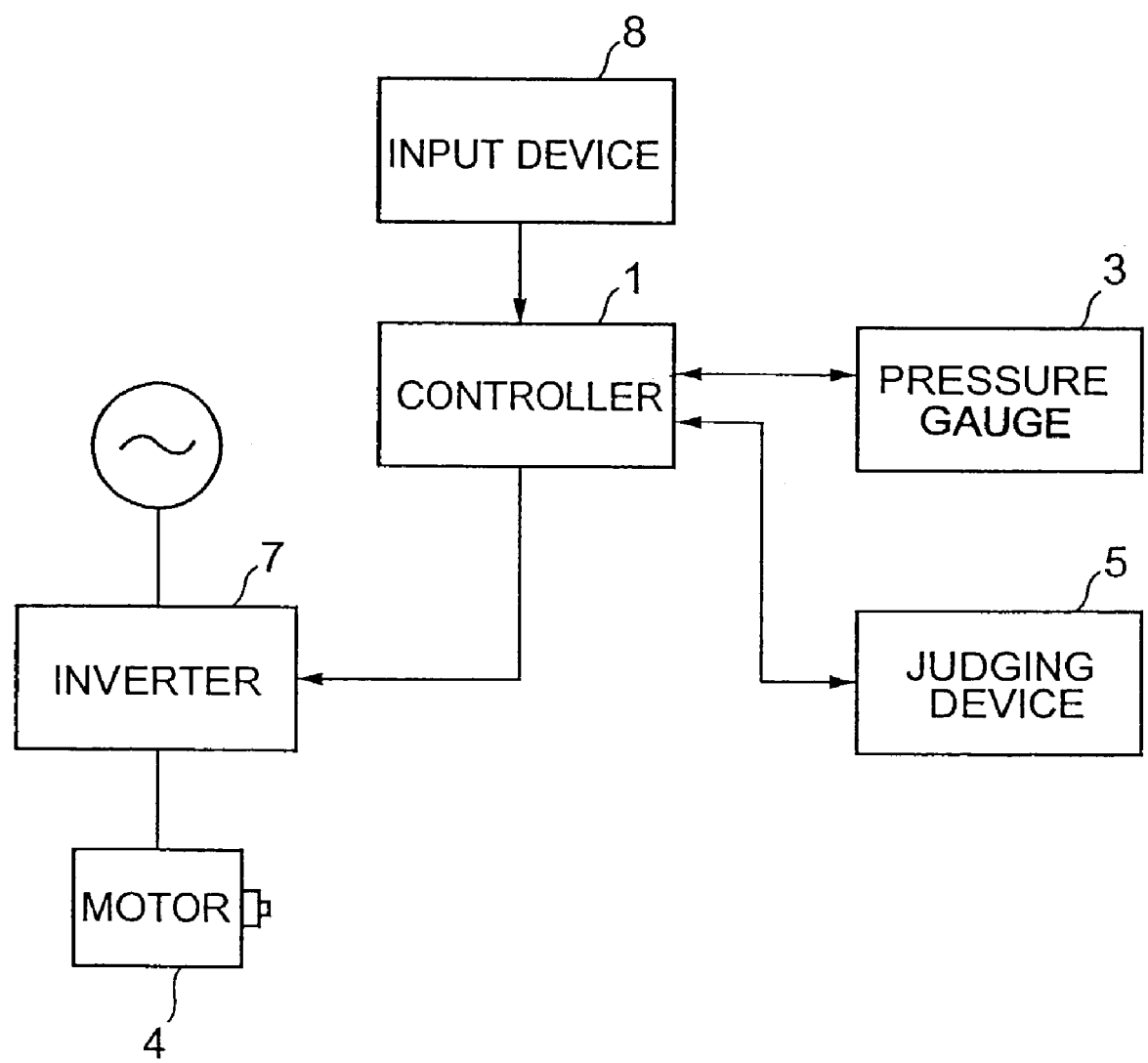
FIG. 3 is a circuit diagram illustrating the configuration of a speed control of a roots blower driving motor in the powdery particle conveying system illustrated in FIG. 2.

Reference numeral 1 designates a controller for controlling the output of the roots blower 2, that is, the speed of the motor 4. As illustrated in FIG. 3, to the controller 1 are connected the pressure gauge 3, a judging device 5, and an input device 8 for designating or changing the reservoir tank 30, to which the powder particles are conveyed. The judging device 5 judges based on a pressure value inside of the conveying pipe 6 at an outlet of the roots blower 2, sent from the pressure gauge 3, as to whether or not the powdery particle conveying system maintains the state in which there is no danger of closure of the conveying pipe. Judgement criteria include whether or not the pressure inside of the conveying pipe 6 tends to be reduced in a predetermined manner according to the speed reduction of the roots blower, that is, whether or not the pressure inside of the conveying pipe 6 reaches a lowest value, or whether or not a fluctuation prognosticative of the closure inside of the conveying pipe occurs in the pressure inside of the conveying pipe 6, that is, whether or not the inside of the conveying pipe 6 is temporarily or partly closed by the powdery particles.

Based on the judgment of the judging device 5, the controller 1 controls the speed of the motor 4 in the roots blower 2 in such a manner as to become a lowest speed within the range in which the state of no danger of the closure inside of the conveying pipe is maintained.

Furthermore, based on the value sent from the judging device 5, the controller 1 changes the speed of the motor 4 to a most proper value at all times. The functions performed by the controller 1 and the judging device 5 can be achieved by a programmable logic controller unit.

Next, explanation will be made on the conveyance of the powdery particles by the roots blower 2.

Assuming that, for example, the reservoir tank 30, to which the powdery particles are conveyed, is the reservoir tank 30 (i.e., B2) located at the position remotest from the roots blower 2, the input device 8 inputs an identification reference B2 of the reservoir tank 30 (i.e., B2), to which the powdery particles are conveyed. The controller 1 outputs a command of a high frequency fh corresponding to the identification reference B2. Furthermore, the respective switch valves 10 of the reservoir tanks 30 (A1 to A4, B1 and C1 to C3) are switched by a mechanism not illustrated, thereby defining only a channel to the reservoir tank 30 (i.e., B2). The inverter 7 receives the frequency command from the controller 1, and then converts the frequency of the power source voltage into a frequency fh so as to supply the frequency fh to the motor 4. Consequently, the motor 4 is rotated at the speed corresponding to the frequency fh, so that a compressed air flow generated by the roots blower 2 is fed to the conveying pipe 6. The powdery particles contained in the hopper 12 are conveyed into the conveying pipe 6 via the rotary valve 14 together with the compressed air flow, and further are conveyed up to the reservoir tank 30 (i.e., B2) by the compressed air flow. The frequency of the power source to motor 4 is maintained, and therefore the motor is initially rotated at a high speed.

After the start of the conveyance, the controller 1 sends a command to gradually reduce the voltage frequency of the power source to the inverter 7, and therefore to reduce the speed of the motor 4. In the meantime, the judging device 5 judges the conveying state of the powdery particles based on the output from the pressure gauge 3. In other words, the judging device 5 monitors whether or not a ratio of a reduction width of the pressure inside of the conveying pipe 6 to a reduction width of frequency of the power source is smaller than a predetermined value, or whether or not a fluctuation prognosticative of the closure inside of the conveying pipe occurs in the pressure inside of the conveying pipe 6. If it is found that the ratio is smaller than the predetermined value or the fluctuation occurs, the judging device 5 judges that the speed of the motor 4 is improper, that is, an intended conveying state cannot be maintained. When the judging device 5 judges that the speed of the motor 4 is improper, the controller 1 sends a command to the inverter 7 to return the conveying state to a proper state, thereby increasing the frequency of the power source voltage so as to increase the speed of the motor 4.

Thus, the conveyance is continued at the frequency at which the intended conveying state can be stably maintained.

In this manner, the power consumption by the roots blower 2 can be saved by reducing the speed of the motor 4 in the roots blower 2 to such an extent that the conveying state can be stably maintained.

In contrast, in the case where the reservoir tank 30, to which the powdery particles are conveyed, is the reservoir tank 30 (i.e., A1) located at a position nearest the roots blower 2, the input device 8 inputs an identification reference A1 of the reservoir tank 30 (i.e., A1). Since a conveying load is small due to a short distance from the roots blower 2 to the reservoir tank 30 (i.e., A1), the intended conveying state can be maintained at a speed of the motor 4 lower than that in the case of the conveyance to the reservoir tank 30 (i.e., B2).

If the intended conveyance can be maintained even though the frequency (50 Hz) of a commercial power source voltage to be applied to the motor 4 is reduced down to 90% in comparison with the reservoir tank 30 (i.e., B2), to which the powdery particles are conveyed, in the case where, for example, the reservoir tank 30, to which the powdery particles are conveyed, is the reservoir tank 30 (i.e., A1), the voltage frequency of the power source can be reduced down to 45 Hz, thereby suppressing the power consumption. This also reduces the output of the roots blower 2, i.e., the generated air quantity, and therefore no excessive dynamic pressure can be applied to the powdery particles, thus reducing the possibility of occurrence of denaturalization or the like of the powdery particles.

Subsequently, a description will be given of experimental examples conducted by the inventors.

The experiment was conducted with respect to a reservoir tank D located at a position approximately 70 meters from the roots blower 2 and another reservoir tank E located at a position approximately 28 meters from the roots blower 2 by using a commercial power source.

The conveyance to the reservoir tank D located remotely from the roots blower needs to be operated at a commercial frequency of 50 Hz since disturbance occurred in the conveyance when the frequency of the power source was reduced.

In contrast, in the case of the conveyance to the reservoir tank E located near the roots blower, the frequency of the commercial power source was gradually decreased from 50 Hz down to 30 Hz by the inverter 7. Even if a current was decreased from 27A down to 18A, there was no large fluctuation in discharge pressure, and therefore the powdery particles could be smoothly conveyed, thereby remarkably lowering power consumption.

Although in the above-described embodiment, the speed of the motor was decreased by reducing the frequency of the power source voltage, thereby saving the power consumption by the motor, the method for changing the speed is not limited to this. Moreover, although the conveying state of the powdery particles was determined based on the pressure value inside of the conveying pipe, the flow rate of the air flow or the conveying speed of the powdery particles may be used as a criterion. In the case where the conveying speed of the powdery particles is used as a criterion, a measuring device capable of detecting the flow rate of a fluid in a solid phase needs to be disposed on the conveying pipe 6. In this case, the measuring device preferably detects in a non-contact manner by an ultrasonic wave or the like.

Next, a powdery particle conveying system in another embodiment according to the present invention will be described in reference to FIG. 4.

Figure 4:
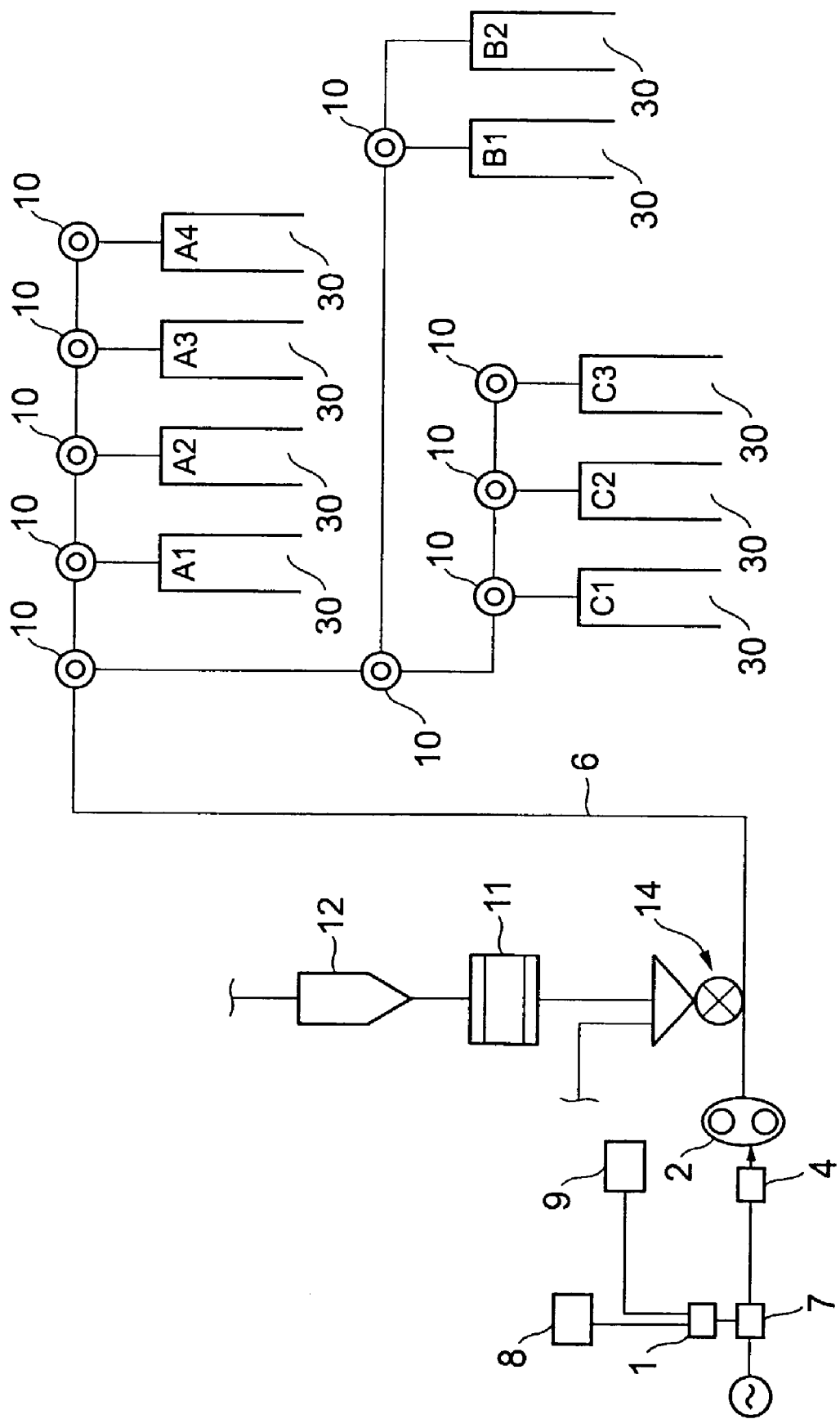
FIG. 4 is a diagram illustrating the general configuration of a powdery particle conveying system in another embodiment according to the present invention; and output of the roots blower 44 is excessive, and therefore forces greater than required are applied to the powdery particles being conveyed, thereby inducing a fear of denaturalization of the powdery particles.
Figure 5:
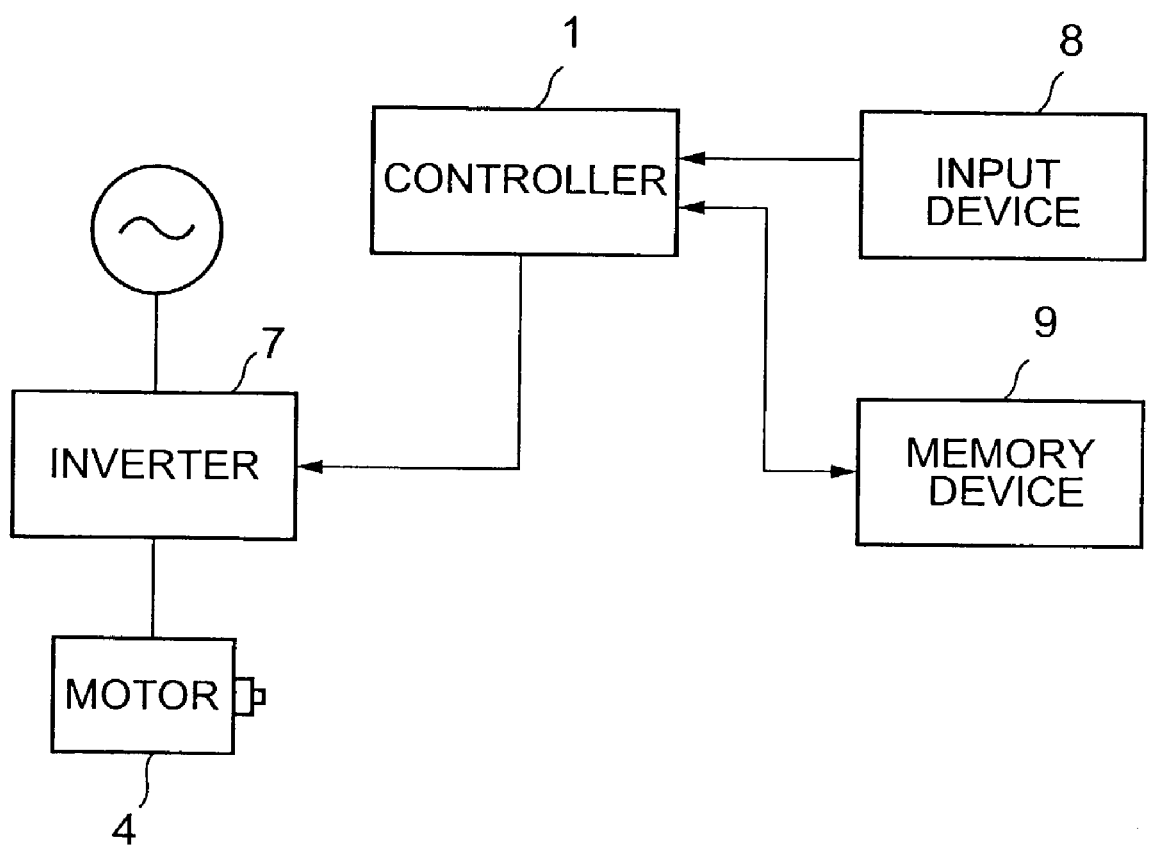

FIG. 4 is a diagram illustrating the general configuration of the powdery particle conveying system in another embodiment. The same reference numerals in FIG. 4 as those in FIG. 2 designate the same components. A difference of the present embodiment from the embodiment illustrated in FIG. 2 is simplification achieved by providing a memory device 9 in place of the pressure gauge 3 and the judging device 5.

Since the basic configuration and basic operation of this system are the same as those in the system described above in reference to FIG. 2, their descriptions will be omitted below but only the difference will be described below.

The memory device 9 stores therein output values (for example, frequencies) of a roots blower 2 with respect to all of reservoir tanks 30.

Explanation will be made below on the conveyance of powdery particles by this system. In the state in which the powdery particles are contained in a hopper 12, first, an input device 8 inputs an identification reference B2 of the reservoir tank 30, to which the powdery particles are conveyed. As described already in the first embodiment, a conveying channel to the reservoir tank 30 (i.e., B2) is defined by switching switch valves 10. Furthermore, a controller 1 reads, from the memory device 9, the output value of the roots blower 2 with respect to the reservoir tank 30 (i.e., B2), that is, the frequency of a power source voltage to be applied to a motor 4 based on the input identification reference. Since the reservoir tank 30 (i.e., B2) is located most remotely from the roots blower 2, the output value, that is, the frequency of the power source voltage with respect to that reservoir tank, is a frequency (50 Hz) itself of the commercial power source. Therefore, the frequency of the commercial power source is applied to the motor 4 as it is, so that the engine speed of the motor 4 becomes maximum. Thereafter, the conveyance is maintained while the commercial frequency is fixed. The powdery particles contained in the hopper 12 are conveyed into a conveying pipe 6, in which a compressed air flow is introduced from the roots blower 2 via a rotary valve 14, and then are smoothly conveyed to the reservoir tank 30 (i.e., B2).

In contrast, in the case where the reservoir tank, to which the powdery particles are conveyed, is a reservoir tank 30 (i.e., A1) near the roots blower 2, a power source frequency with respect to the reservoir tank 30 (i.e., Al) is stored in the memory device 9 as, for example, 90% of a commercial frequency since a conveying load is small owing to a short distance from the roots blower 2 to the reservoir tank 30 (i.e., A1). Thus, the controller 1 gives instructions to drive the motor 4 via an inverter 7 at 90% of the commercial frequency, that is, at 45 Hz. The controller 1 drives the motor 4, and thereafter supplies electric power while maintaining the frequency.

In this manner, the system is operated by reducing the frequency of the power source voltage to be applied to the motor 4, thereby saving the power consumption by the motor 4. Consequently, the speed of the motor 4 is reduced, so that the output of the roots blower 2, that is, the generated air quantity, is reduced. However, since the conveying load is small owing to the short distance from the roots blower 2 to the reservoir tank 30 (i.e., A1), the powdery particles are smoothly conveyed to the desired reservoir tank 30 (i.e., A1). Moreover, the powdery particles are conveyed at an adequate air flow rate, and therefore no excessive dynamic pressure can be applied to the powdery particles, thereby preventing any occurrence of denaturalization or the like caused by the dynamic pressure or the like.

Likewise in the foregoing embodiment, the present inventor conducted conveyance experiments with respect to the reservoir tanks located at two different positions, that is, a reservoir tank-D located at a position approximately 70 meters from the roots blower and another reservoir tank E located at a position approximately 28 meters from the roots blower. The conveyance to the reservoir tank D located remotely from the roots blower needs to be operated at a commercial frequency of 50 Hz since disturbance occurred in the conveyance when the power source frequency was reduced. In this manner, the operation at the commercial frequency of 50 Hz arose with no problem.

In contrast, in the case of the conveyance to the reservoir tank E located near the roots blower 2, the frequency of the power source voltage to be applied to the motor 4 was decreased from 50 Hz down to 30 Hz. As a result, even if a current value was decreased from 27A down to 18A, the powdery particles could be conveyed without any trouble, thereby remarkably saving the power consumption by the motor.

Although in the above-described embodiment the change of the speed of the roots blower has been exemplified by the change of the frequency of the power source voltage with respect to the motor, it is not limited to this, and the change may be carried out by another method.

Furthermore, although the pressure inside of the conveying pipe has been used in judging whether or not the powdery particle conveying state is normal, the flow rate of the compressed air current or the flow rate of the powdery particles inside of the conveying pipe may be measured.

Although in the above-described embodiment the conveying load during the conveyance of the powdery particles has been exemplified by the conveyance distance, other examples of the conveying load include the conveying quantity or kind of powdery particles to be conveyed (for example, flour, wheat bran, flour grains and the like) or the magnitude of the conveying load such as a pressure loss on the conveying channel (for example, the bend of the conveying channel, the number of switch valves, the property of the inner surface of the conveying pipe, i.e., a surface roughness, and the like). The same concept can be adopted.

Additionally, it is understood that the present invention can be applied to a system for conveying or transporting not only the powdery particles but also other powdery particulate materials to different positions.

In the system for conveying the powdery particles by the use of the roots blower to be driven by the motor according to the present invention, the electric power to be supplied to the roots blower driving motor is reduced according to the conveying load within the range in which the secure conveyance can be carried out, thereby preventing the wasteful energy consumption required for the conveyance. Furthermore, in this manner, the powdery particles can be conveyed with the proper output, so that no excessive pressure can be applied to the powdery particles, thus preventing any occurrence of denaturalization or the like of the powdery particles.

What is claimed is:

1. A powdery particle conveying system in which an air current is formed by rotating a roots blower driving motor and powdery particles are pneumatically transported on the air current inside a conveying pipe to a selected one of a plurality of reservoir tanks located at different locations in the same site, wherein a discharge pressure of the roots blower is measured, the system including a control means for controlling a speed of rotation of the motor on the basis of the measured discharge pressure in such a manner that a transporting state of the powdery particles can be maintained in the conveying pipe without settling out.

2. A powdery particle conveying system of pressure type according to claim 1, wherein the speed of rotation of the roots blower driving motor is controlled by changing a frequency of a power source for the driving motor through an inverter.

3. A method of transporting powdery particles from a storage facility to a selected one of a plurality of tanks located at varying distances from the storage facility, the method comprising operatively coupling a motor driven roots blower to the storage facility and the tanks so that the powdery particles can be transported from the storage facility to the tanks;

selecting one of the tanks to which the powdery substance is to be transported;

activating the roots blower to initiate a flow of powdery particles to the selected tank;

determining a discharge pressure for the powdery particles to the selected tank below which there is a danger that powdery particles will settle out of the flow and obstruct the flow; and setting the substantially lowest electric power input to the motor of the roots blower which will cause the roots blower to maintain a sufficient discharge pressure to the selected tank to prevent powdery particles from settling out.

4. A method according to claim 3 wherein setting the lowest electric power input comprises changing a frequency of an electric power source driving the motor.

5. A method according to claim 3 wherein activating the roots blower comprises supplying the motor of the roots blower with electric power which is substantially above the lowest electric power input to the motor which will prevent powdery particles from settling out, and wherein setting the lowest electric power input comprises gradually lowering the electric power input to the motor until the lowest electric power input has been reached.

6. A method according to claim 3 including monitoring the flow of powdery particles while powdery particles are being transported to the selected tank, and wherein setting the lowest electric power input comprises adjusting the lowest electric power input in response to changes in the flow of powdery particles to the selected tank observed during monitoring.

7. Apparatus for transporting powdery particles from a storage facility to a selected one of a plurality of tanks located at varying distances from the storage facility, comprising a motor driven roots blower operatively coupled to the storage facility and the tanks and generating a gaseous flow with a discharge pressure for transporting the powdery particles from the storage facility to the tanks;

means for selecting one of the tanks to which the powdery substance is to be transported; and a controller coupled to the roots blower and controlling a rotational speed of the roots blower on the basis of the discharge pressure at which a transporting state to the selected tank is maintained which prevents powdery particles from settling out and which provides the substantially lowest electric power input to the roots blower.

8. Apparatus for transporting powdery particles with an air stream through a conveying pipe from a storage facility to a selected one of a plurality of tanks which are spaced apart and located at varying distances from the storage facility, the apparatus comprising a motor driven roots blower at the storage facility that is fluidly coupled to the tanks and generates a discharge pressure for the air stream for transporting the powdery particles from the storage facility to the tanks;

a flow selector for fluidly connecting any one of the tanks with the roots blower; and a controller for controlling a speed of rotation of the roots blower as a function of the discharge pressure so that a transporting state is maintained at all times at which powdery particles will not settle out of the air stream.

* * * * *